(12) United States Patent
Tsunemi (10) Patent No.: US 6,327,337 B1
(45) Date of Patent: Dec. 4, 2001

(54) METHOD AND APPARATUS FOR DETERMINING INCIDENT POSITION OF X-RAY DETECTED BY USE OF CCD (75) Inventor: Hiroshi Tsunemi, Suita (JP)

(73) Assignee: Japan Science and Technology Corporation (JP)

( * ) Notice: Subject to any disclaimer, the term of this patent is extended or adjusted under 35 U.S.C. 154(b) by 0 days.

(21) Appl. No.: 09/446,385
(22) PCT Filed: Mar. 25, 1999
(86) PCT No.: PCT/JP99/01530
§ 371 Date: Dec. 21, 1999
§ 102(e) Date: Dec. 21, 1999
PCT Pub. Date: Mar. 25, 1999

(30) Foreign Application Priority Data

Apr. 28, 1998 (JP) .................................................. 10-117627

(51) Int. Cl.[7] ..................................................... H05G 1/64
(52) U.S. Cl. ........................................... 378/98.8; 378/164
(58) Field of Search .................................. 378/98.8, 164, 378/205

(56) References Cited

PUBLICATIONS

Hiraga et al., "How big are charge clouds inside the charge-coupled device produced by x-ray photons?," Japanese Journal of Applied Physics, Part 1: Regular Papers, Short Notes & Review Papers—Aug. 1998—vol. 37, Issue 8 pp. 4627–4631.*

Pivaroff, M. et al., "Measurement of the Subpixel Structure of AXAF CCD's", IEEE Transactions on Nuclear Science, vol. 45, No. 2, Apr. 1998.*

Tsunemi, H. et al., "Direct Measurements at the Sub–pixel Level of the X–ray Detection Efficiency of the CCD on board the ASCA satellite, " Nuclear Science Symposium, 1997. IEEE, 1997 pp.: 592–596 vol. 1.*

\* cited by examiner

Primary Examiner—Robert H. Kim
Assistant Examiner—Courtney Thomas
(74) Attorney, Agent, or Firm—Lorusso & Loud (57) ABSTRACT

A parallel X-ray beam generated from an X-ray generator is radiated onto a CCD of a CCD camera via a metal mesh disposed in front of the CCD. In order to detect the X-ray, a multi-pitch metal mesh (11) is disposed as the metal mesh. The incident position of the X-ray is determined on the basis of a ratio between a primary electron cloud produced by the X-ray spread over a plurality of pixels and a portion of the cloud existing in each of the plurality of pixels.

6 Claims, 6 Drawing Sheets

BOTTOM SPLIT

TOP SPLIT

LEFT SPLIT

RIGHT SPLIT

FIG. 9(a)   FIG. 9(b)

THREE-PIXEL EVENT

FOUR-PIXEL EVENT

METHOD AND APPARATUS FOR DETERMINING INCIDENT POSITION OF X-RAY DETECTED BY USE OF CCD

TECHNICAL FIELD

The present invention relates to a method and apparatus for determining the incident position of an x-ray detected by use of a charge-coupled device (hereinafter referred to as a "CCD").

BACKGROUND ART

CCDs for directly detecting X-rays are now widely used, particularly in the field of astronomy (see G. W. Frazer: "X-Ray Detectors in Astronomy," Cambridge University press (1989) 208; and B. E. Burke, R. W. Mountain, P. J. Deniels, M. J. Cooper, and V. S. Dolat: IEEE Trans. Nuclear Sci. 41 (1994) 375).

A CCD is an integral-type sensor which can increase the resolution of an image to a level corresponding to pixel size. If the flux of incident X-rays can be reduced to such a level that primary electron clouds produced by X-ray photons do not overlap each other, in addition to an X-ray image, an X-ray energy spectrum can be obtained.

At present, a CCD is widely used as an X-ray photon counter, particularly in the field of astronomy. When the flux of incident X-rays is reduced to such a level that primary electron clouds produced by X-ray photons do not overlap each other, in addition to an X-ray image, an X-ray energy spectrum can be obtained.

Recently, the present inventors proposed a new technique, by which the X-ray response of a CCD can be obtained with subpixel resolution (Japanese Patent Application No. 9-82444). The new technique employs a metal mesh placed in proximity to a CCD, and a parallel X-ray beam. The mesh has a large number of small holes with periodic spacing, the spacing being equal to the CCD pixel size. Hereinafter, such a mesh is referred to as a "single-pitch mesh." Since the position of an input X-ray can be determined with subpixel resolution, X-ray response can be investigated in detail.

Figure 1:
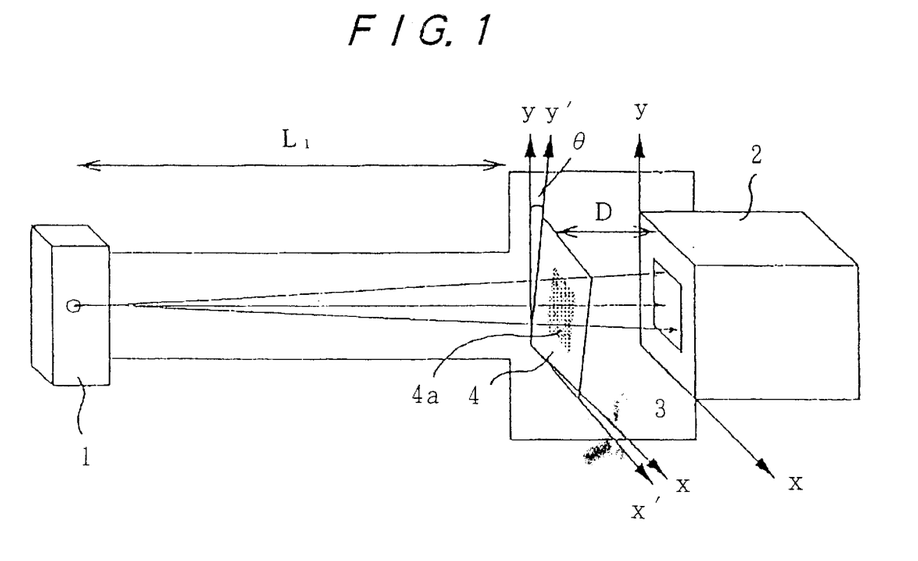
FIG. 1 shows a view showing the overall structure of an apparatus for measuring X-rays detected by use of a CCD.
Figure 2:
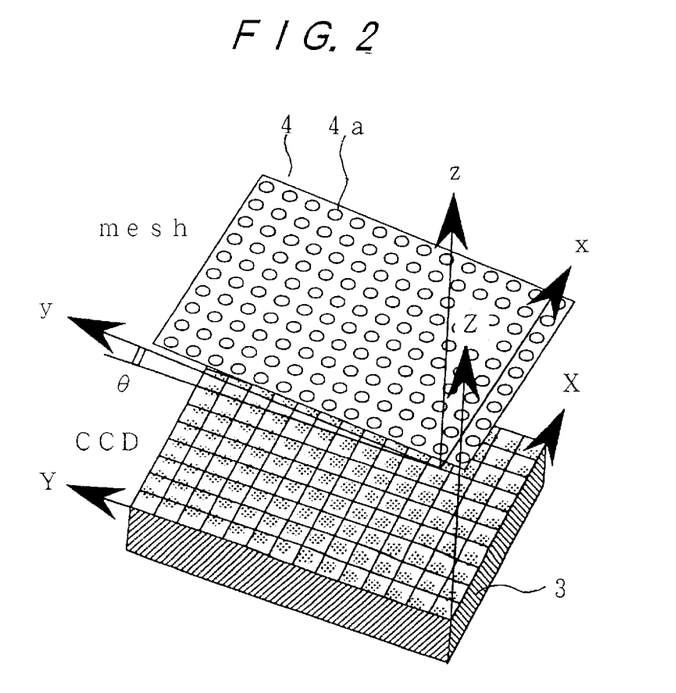
FIG. 2 is a schematic view showing an experiment performed for a single-pitch mesh.

FIG. 1 shows the overall structure of an apparatus for measuring X-rays detected by use of a CCD. FIG. 2 is a schematic view showing an experiment performed by use of a single-pitch mesh.

In FIGS. 1 and 2, reference numeral 1 denotes an X-ray generator, 2 denotes a CCD camera, 3 denotes a CCD, 4 denotes a single-pitch metal mesh, and 4a denotes holes of the single-pitch metal mesh.

As shown in FIG. 2, the metal mesh 4 having periodically spaced holes is placed in close proximity to the surface of the CCD 3. The mesh 4 is placed parallel to the surface of the CCD 3 and tilted by a small angle θ with respect the pixel axis. A parallel X-ray beam is radiated normal to the surface of the CCD 3. The X-rays passing through the mesh holes 4a reach the CCD 3. The position of X-ray interaction (hereinafter referred to as an "X-ray interaction position") is restricted by the mesh hole 4a. An X-ray event whose interaction position is far from a pixel boundary should take place in a pixel where a mesh hole 4a is located at the center thereof. In such a situation, a single-pixel event usually occurs.

Meanwhile, an X-ray event whose interaction position is close to a pixel boundary takes place in a pixel which has more than two hole shadows. In this case, a split event occurs. When a single-pitch mesh is used, the single-pixel event and the split event cannot be distinguished from each other, because the mesh holes 4a have a fixed size, and spacing between holes is equal to the inter-pixel distance. Therefore, even when a pixel at which an X-ray event occurs can be determined, the hole through which the X-ray enters cannot be determined.

DISCLOSURE OF THE INVENTION

When X-rays are detected by use of a CCD, the X-ray energy can be measured as well, if the X-rays are measured on a ray-by-ray basis. In this case, a primary electron cloud (consisting of several hundreds to several thousands of electrons) formed due to an incident X-ray spreads to some degree. If a pattern of such a spread can be determined so as to determine the shape, it becomes possible to find how a signal is determined on the basis of the incident position of an X-ray, to thereby enable precise determination of the incident position.

In view of the foregoing, an object of the present invention is to provide a method and apparatus for determining an incident position of an X-ray detected by use of a CCD, which method and apparatus enable the incident position of an X-ray to be determined with sub-pixel resolution.

To achieve the above object, the present invention provides the following methods and apparatuses.

(1) A method of determining an incident position of an X-ray detected by use of a CCD of a CCD camera onto which a parallel X-ray beam generated from an X-ray generator is radiated via a metal mesh disposed in front of the CCD, characterized in that a multi-pitch metal mesh is disposed as the metal mesh; and the incident position of the X-ray is determined on the basis of a ratio between a primary electron cloud produced by the X-ray spread over a plurality of pixels and a portion of the cloud existing in each of the plurality of pixels.

(2) The method as described in (1) above, further characterized in that the accuracy in determining the incident position of an X-ray is about one-tenth of the pixel size of the CCD.

(3) The method as described in (1) above, further characterized in that an interaction position is determined from an event pattern on the basis of the center of gravity of an X-ray event.

(4) The method as described in (3) above, further characterized in that the center of gravity of an X-ray event is obtained on the basis of an output signal of a corresponding pixel.

(5) An apparatus for determining an incident position of an X-ray detected by use of a CCD of a CCD camera onto which a parallel X-ray beam generated from an X-ray generator is radiated via a metal mesh disposed in front of the CCD, characterized by comprising: an X-ray generator for obtaining a parallel X-ray beam; a multi-pitch metal mesh disposed in front of the CCD and adapted to receive the parallel X-ray beam; a CCD camera for photographing the CCD; and means for determining the incident position of the X-ray on the basis of a ratio between a primary electron cloud produced by the X-ray spread over a plurality of pixels and a portion of the cloud existing in each of the plurality of pixels.

(6) The apparatus as described in (5) above, further characterized in that the multi-pitch metal mesh has a large number of circular holes disposed at a pitch four times the pixel size of the CCD.

In the present invention, when an X-ray signal spreads over two pixels, the signal is distributed according to the incident position of the X-ray and the shape of the electron cloud. Through an experiment using a mesh, the present inventors investigated how an X-ray signal spreads over two pixels depending on the incident position of the X-ray, and found a method of accurately determining the incident position of the X-ray on the basis of the ratios of portions spreading over the two pixels. As a result, the accuracy in determining the incident position can be improved to one-tenth of the pixel size (variance).

BEST MODE FOR CARRYING OUT THE INVENTION

An embodiment of the present invention will next be described in detail with reference to the drawings.

Figure 3:
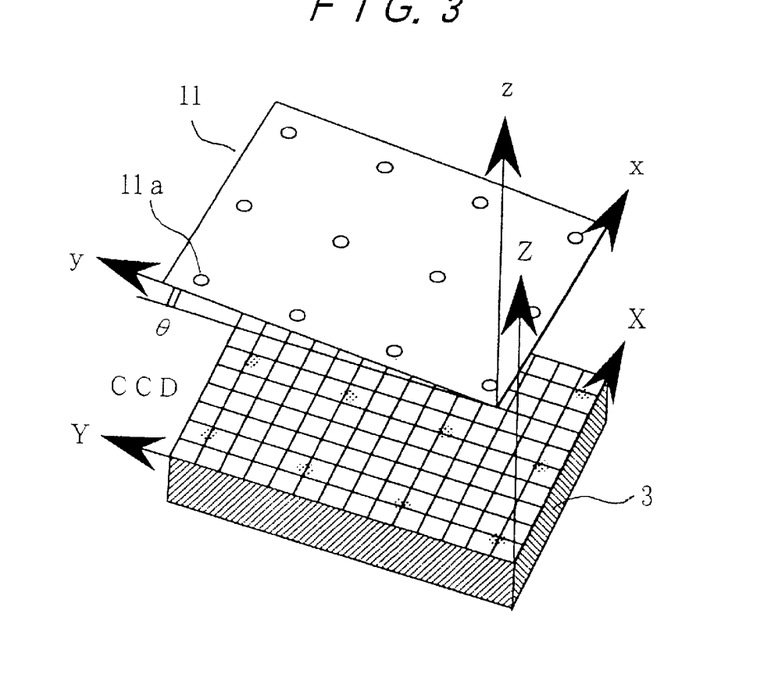
FIG. 3 is a view relating to an embodiment of the present invention and showing an apparatus for determining an incident position of an X-ray detected by use of a CCD, in which a multi-pitch mesh is used.

FIG. 3 is a view showing an embodiment of the present invention; i.e., an apparatus for determining an incident position of an X-ray detected by use of a CCD, in which a multi-pitch mesh is used. In FIG. 3, dotted regions represent hole shadows.

The present embodiment employs a "multi-pitch mesh" formed of metal; i.e., a multi-pitch metal mesh 11. In the multi-pitch metal mesh 11, pitch of holes 11a is n times the pixel pitch of a CCD 3, where n is an integer. In the present embodiment, an experiment was performed while the hole pitch was set to 4 times the CCD pixel size. Results of the experiment revealed that, due to employment of a large pitch, no pixel has two or more hole shadows, and a large number of pixels have no hole shadows.

The multi-pitch mesh 11 used in the present embodiment is made of copper and has a thickness of 10 $\mu$m. The holes 11a have a diameter of 3.4 $\mu$m and are disposed at a pitch of 4.8 $\mu$m. A mesh holder was designed to be placed 1 mm above the CCD surface. The mesh was tilted by about −1° from the pixel axis, so that a moire pattern could be obtained.

As in an experiment performed with a conventional mesh, a 21 m-long X-Ray beam line was used. A voltage of about 5 kV was applied to an X-ray generator [UltraX-18 (RIGAKU)].

Figure 4:
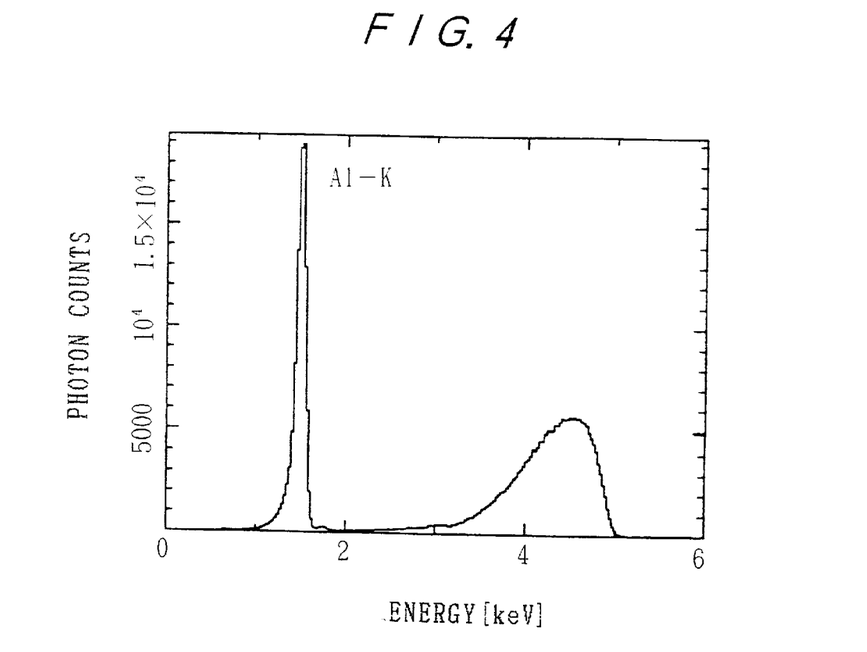
FIG. 4 is a graph relating to the embodiment of the present invention and showing an X-ray spectrum.

FIG. 4 shows the obtained X-ray spectrum. The vertical axis represents photon count, and the horizontal axis represents energy (keV).

The transmission of 10-$\mu$m-thick copper foil is $10^{-3}$ at 3 keV and is lower than this at lower X-ray energies. Therefore, X-rays having energies higher that 3 keV penetrate the copper foil, while all Al—K X-rays reach the CCD through the mesh holes. Therefore, through selection of the Al—K X-rays, only X-rays passing through the mesh holes can be captured.

A CCD chip, N11-5-5AON-2 (product of Hamamatsu Photonics), having a pixel size of 12 $\mu$m$^2$ was used. The CCD chip was cooled to −60° C. The CCD camera system was equipped with a mechanical shutter (60 $\mu$m-thick stainless steel) so as to block the Al—K X-rays. The system can record images every 20 sec (including the time required for transferring data to the hard disk of a computer). The exposure time was set to about 5 sec in order to maximize the number of isolated X-ray photons detected by the CCD. The system was operated in this manner for about 20 h, so that about 1×10$^5$ single events of Al—K X-rays were obtained.

Figure 5:
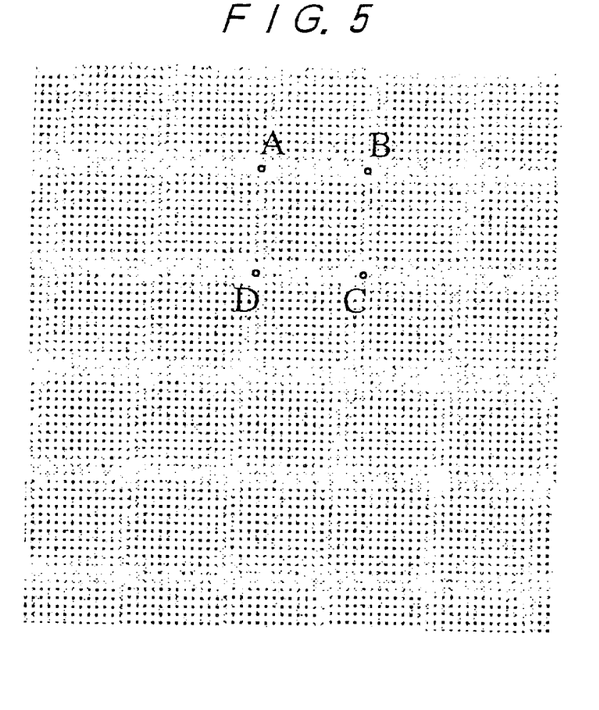
FIG. 5 is an illustration relating to the embodiment of the present invention and showing a distribution of single events of Al—K X-rays which were obtained through use of a mesh having a hole pitch four times the size of pixels.

FIG. 5 shows distribution of single events of Al—K X-rays which were obtained through use of a mesh having a hole pitch four times the pixel size.

This distribution is quite different from that obtained by use of a single-pitch mesh. Single events appear roughly every 4×4 pixels, due to employment of the multi-pitch mesh.

A moire pattern obtained in an experiment performed by use of a single-pitch mesh is a direct enlargement of a pixel image. Therefore, a pixel image of subpixel resolution can be obtained through analysis of a moire image if the moire pattern is sufficiently large and the intensity of an X-ray beam is uniform over the moire pattern.

The present invention employs a universal method which functions well even if the moire pattern is too small to be noticed.

In the method according to the present invention, a moire pattern does not directly represent a corresponding pixel image. In the conventional method performed by use of a single-pitch mesh, the CCD pixel is assumed to have a perfect square shape and the distributed mesh holes are assumed to be perfectly spaced. In the present invention, a possible effect caused by distortion of mesh hole distribution is taken into consideration.

The restoration method is described in detail as follows.

The CCD pixel coordinate X is expressed by equation (1):

$$X = C \begin{pmatrix} 1+a & 0 \\ 0 & 1+b \end{pmatrix} \begin{pmatrix} \cos\theta & -\sin\theta \\ \sin\theta & \cos\theta \end{pmatrix} \times x + X_{off} \quad (1)$$

where x denotes the coordinate of a mesh hole, C is a coefficient of the multi-pitch mesh (4 in the present embodiment), a and b are expansion coefficients for the mesh hole coordinate, $\theta$ is tilt angle, and $X_{off}$ is an offset. The expansion coefficients are introduced for several reasons; i.e., X-ray beam divergence, a difference in thermal contraction between the mesh and the CCD, and the accuracy of the mesh and the mesh holder. Coefficients a and b (a~0, b~0) are introduced in order to take into account the effect of possible differences in mesh hole spacing on the CCD pixel coordinate. The output of the nth pixel of the CCD, Dn, is expressed as follows:

$$D_n = \int_{nth\ pixel} M(x) E(X) dX \quad (2)$$

where M(x) denotes the transmission of the mesh, and E(X) is the detection efficiency of the CCD.

The transmission of the mesh is expressed by equation (3):

$$M(x) = \int H(x') L(x-x') dx' \quad (3)$$

$$H(x) = \begin{cases} 1 & (|x| < r) \\ \text{metal transmission} \sim 0 & (|x| > r) \end{cases} \quad (4)$$

$$L(x) = \sum_{n=\text{integer lattice}} \delta(x-n) \quad (5)$$

where H(x) is the typical shape of the mesh hole, L(x) denotes the position of the hole on the mesh, and r is the effective radius of the hole. In the employed experimental setup, r is set to about 2 $\mu$m in consideration of diffraction of Al—K X-rays. Since the holes are disposed at a constant pitch, equation (5) is obtained.

When values are assumed for a, b, $\theta$, and $X_{off}$, a pixel image can be restored. The precise values for these parameters can be obtained through search of a set of values which produce the largest variance in the restored image. In the case of a single-pitch mesh, $X_{off}$ is used for mere offsetting in the restored image, and therefore its role is not important.

This is due to the fact that each pixel has its corresponding mesh hole 4a, as shown in FIG. 2. In contrast, in the case of a multi-pitch mesh according to the present invention, there are many pixels above which no mesh hole 11a is present, as shown in FIG. 3. Therefore, even if precise values are selected for a, b, and $\theta$, a precise value must be specified for $X_{off}$ in order to enable construction of the restoration image by use of pixels corresponding to the mesh holes.

From a practical point of view, identifying a set of true values for the parameters is a rather complicated problem. Furthermore, there are many alias values that produce a similar moire pattern. Next, a method of obtaining a, b, $\theta$, and $X_{off}$ from an image will be described.

In general, X can be measured precisely, but x cannot be measured. Here, a method for estimating rough values will be described. FIG. 5 shows a portion of a raw image (250×250 pixels) obtained by use of single events. Since a multi-pitch mesh is used, single events appear roughly every 4×4 pixels.

Let ABCD represent one element of the moire pattern. The vector AB is represented by X on the CCD coordinate and by x on the mesh coordinate, as follows:

$$(1+a)^2 = (X^2+Y^2)/(x^2+y^2), \text{ and } \tan\theta = (Yx-Xy)/(Xx+Yy).$$

Since the vector AB denotes one element of the moire pattern, the following equation is expected to hold:

$$X - x = \begin{pmatrix} X \\ Y \end{pmatrix} - \begin{pmatrix} x \\ y \end{pmatrix} = \begin{pmatrix} \pm 1 \\ 0 \end{pmatrix} \text{ or } \begin{pmatrix} 0 \\ \pm 1 \end{pmatrix} \quad (6)$$

In total, given the assumptions a, $\theta \sim 0$, four possibilities exist. These are:

$$(a, \theta) \approx \left( \frac{\pm X}{X^2+Y^2}, \frac{\mu Y}{X^2+Y^2} \right), \text{ or } \left( \frac{\mu Y}{X^2+Y^2}, \frac{\pm X}{X^2+Y^2} \right) \quad (7)$$

Similarly, the same relationship can be obtained for (b, $\theta$) by letting the vector AD be represented by X and x.

The values of a and b are unknown, whereas the value of $\theta$ is known. When values are assumed for a, b, $\theta$, and $X_{off}$, the pixel image can be restored. The precise values for these parameters are obtained through search of values which produce the largest variance in the restored image. From the data shown in FIG. 5, the following values are obtained:

$$X_{AB} = \begin{pmatrix} 50.9 \\ -0.7 \end{pmatrix} \text{ and } X_{AD} = \begin{pmatrix} -4.4 \\ -50.3 \end{pmatrix} \quad (8)$$

In the present embodiment, $\theta$ is set to around $-1°$. In the experimental setup, the temperature of the mesh was presumed to be substantially equal to that of the CCD. Therefore, a and b are presumed to be about $-1\times10^{-3}$, in consideration of both beam divergence and thermal contraction. Therefore, for an image having the maximum variance, a value for a was searched in a region around $-1\times10^{-3}$, a value for b was searched in a region around $-1\times10^{-3}$, and a value for $\theta$ was searched in a region around $-1°$. Even when values are assumed for thee parameters, a precise value for $X_{off}$ ($0 < X_{off}, Y_{off} < 4$) must be specified. The value for $X_{off}$ is determined such that the number of X-ray events contributing to image restoration is maximized.

In this way, the image variance was maximized at a $=-0.5\times10^{-3}$, $=-1.3\times10^{-3}$, $\theta=-1.15°$, $X_{off}=2.05$, and $Y_{off}=0.55$. These values were used for obtaining a restoration image, which will be described hereinafter. From the above, it is noticed that the value for a differs from the value for b. This implies that either the hole mesh spacing or the CCD pixel spacing along the x axis is $0.8\times10^{-3}$ longer than that along the y axis.

Next, data analysis will be described.

(1) Restoration of Images for Various Types of X-ray Events

Figure 6:
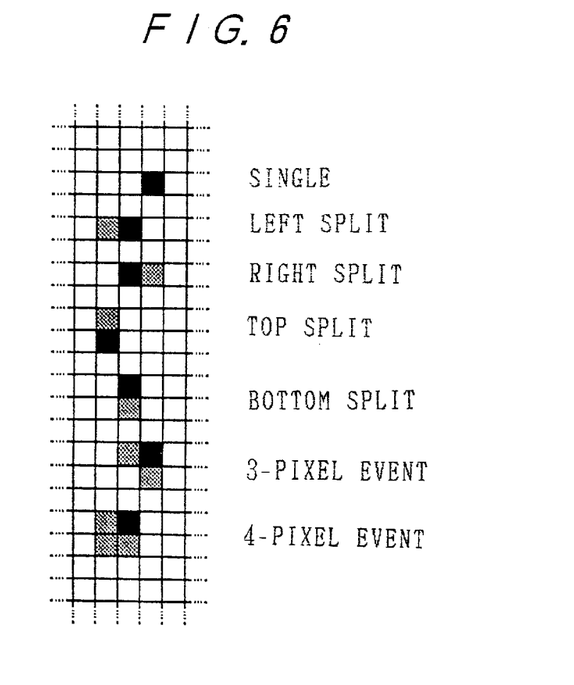
FIG. 6 is an illustration relating to the embodiment of the present invention and showing some examples of X-ray event patterns generated on a CCD.

The present embodiment employs a method which is used in the ASCA satellite and in which X-ray events are classified. First, a pixel whose output is greater than an event threshold ($T_{event}$) is selected. If the pixel output is greater than the event threshold ($T_{event}$) and is the local maximum (its output is greater than those of adjacent pixels), the pixel is called the "X-ray pixel." The X-ray pixel is considered to be the interaction position of the X-ray. X-ray events are classified according to the number of pixels whose output are greater that a particular "split threshold." Some examples are shown in FIG. 6.

Figure 7:
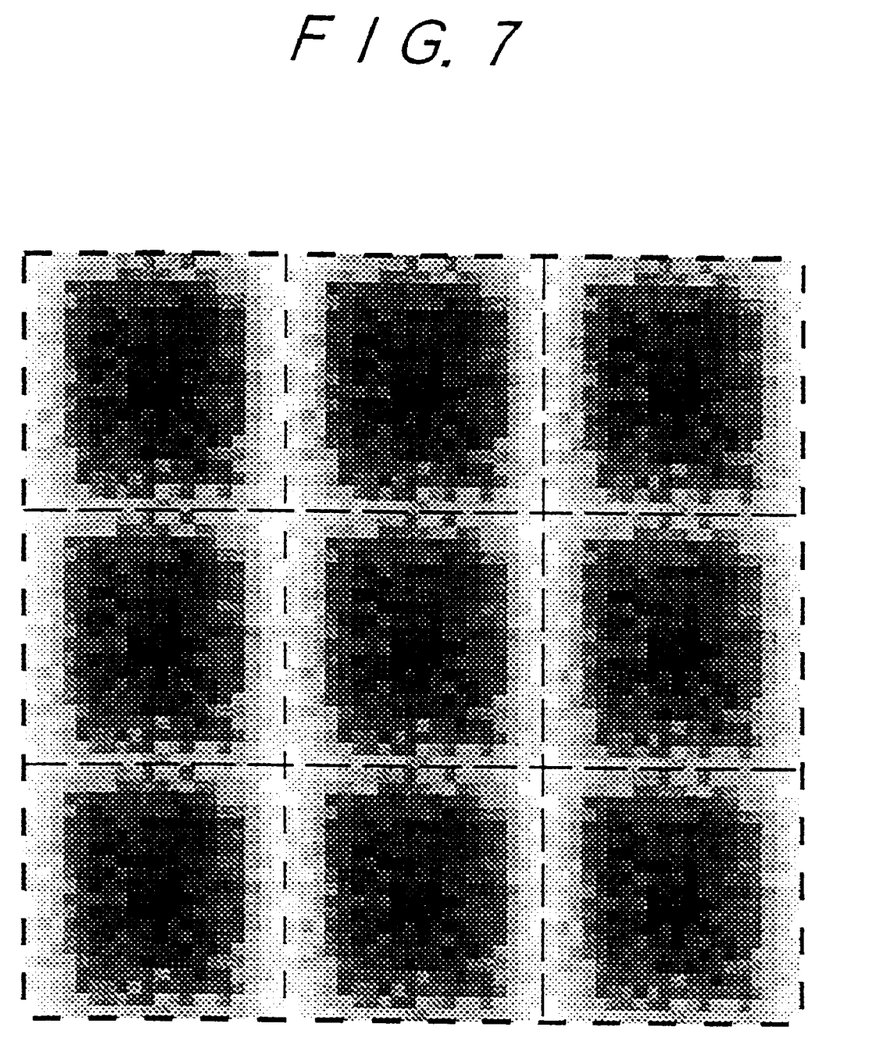
FIG. 7 is an illustration relating to the embodiment of the present invention and showing X-ray intensity maps for single events having a subpixel resolution of 3×3.

As shown in FIG. 7, a restored image of the "representative pixel (RP)" was obtained by use of single events. In FIG. 7, 3×3 RPs are reproduced. Pixel boundaries are indicated by dashed lines. FIG. 7 clearly shows that a single event occurs when the interaction position of the X-ray is well separated from the pixel boundary. The dark region represents the convolution of the effective hole size and the region where X-rays form single events. The width of the boundary region where no single event occurs depends on both the primary electron size and the mesh hole size.

Next, two-pixel events are classified according to their patterns. In two-pixel events, two adjacent pixels have outputs greater than $T_{split}$. The higher-output pixel is called the event pixel, whereas the lower output pixel is called the split pixel. Therefore, as shown in FIG. 6, four types of split events occur according to the position of the split pixel; i.e., a left split event, a right split event, a top split event, and a bottom split event. For each of the four types of split events, an RP was restored.

Figure 8:
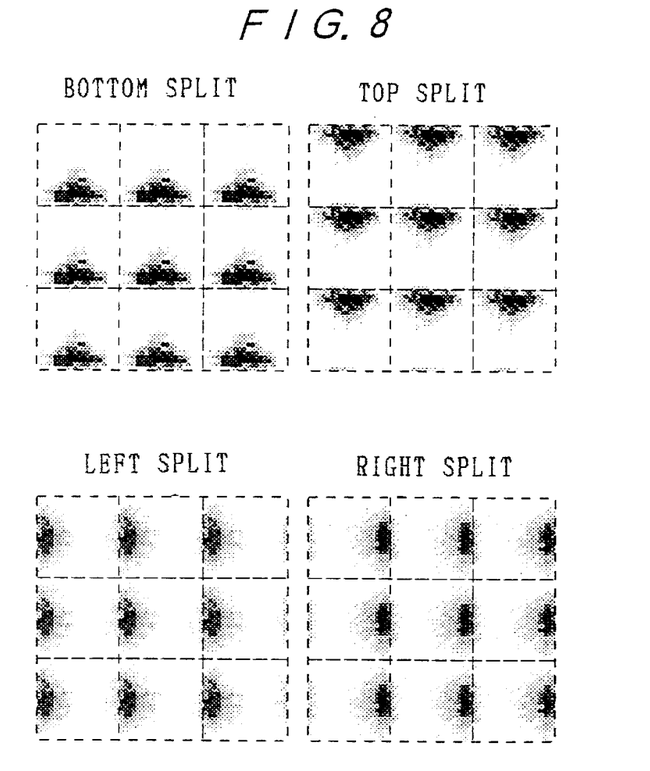
FIG. 8 is an illustration relating to the embodiment of the present invention and showing raw images for the case of split two-pixel events.

FIG. 8 shows RPs for four types of two-pixel events. As is understood from FIG. 8, clear differences exist among the four types. A right split event occurs when an X-ray enters the right boundary portion of a pixel where the primary charge easily splits onto the adjacent right pixel. In contrast, a left split event occurs when an X-ray enters the left boundary portion of a pixel. Similar results can be seen for vertically split two-pixel events.

Figure 9A:
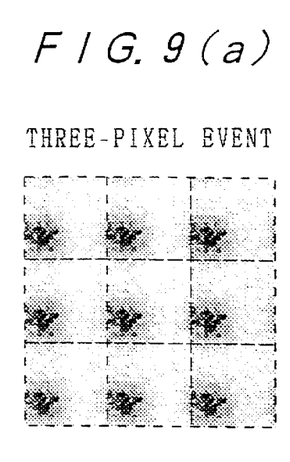
FIGS. 9(a) and 9(b) are illustrations showing data of the events shown in FIG. 6.
Figure 9B:
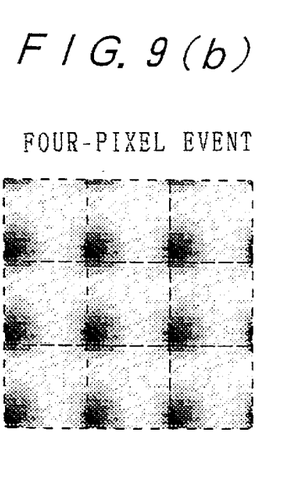

Similarly, 3- or 4-pixel events are classified according to their patterns. As can be easily seen, a 3- or 4-pixel event occurs when an X-ray enters a corner portion of a pixel. FIGS. 9(a) and 9(b) show RPs for 3-pixel events and 4-pixel events, respectively. There are shown events whose event pixel is located in an upper right portion of the X-ray pattern, and both 3- and 4-pixel events were observed. The other three possible types show quite similar images. FIGS. 9(a) and 9(b) clearly show that when an X-ray enters very close to a corner of a pixel, the primary charge splits into a diagonal pixel. It is to be noted that the events can be classified in more detail than in the case of the conventional technique, which is one of the advantages of the multi-pitch mesh experiment which cannot be exhibited by a single-pitch mesh experiment.

(2) Specification of the Interaction Position of X-rays

Use of the multi-pitch mesh enables unambiguous specification of the interaction position of an X-ray.

Until now, a local maximum pixel (event pixel) has been considered to be the interaction position of an X-ray. In the present invention, the distance between an event pixel and a true interaction position (hole position) can be measured.

FIGS. 10(a)–10(d) shows, by means of solid lines, event distribution $D_{event}$ according to the distance between the event pixel location and the true interaction position. This figure shows an uncertainty when the event pixel location is considered to be the interaction position of the X-ray.

For single events, the uncertainties of $D_{event}$ are smaller than 0.5 pixel size. This means that the single event must occur at the pixel which the X-ray enters.

In contrast, the uncertainties of $D_{event}$ for two-pixel split events have two peaks indicating larger uncertainties than those of single events. When an X-ray enters near the pixel boundary, the charge will evenly split into two pixels. In such a case, the event pixel does not show the X-ray interaction position precisely. Therefore, it can be considered that the event pixel represents the X-ray interaction position for single events and that this does not hold true in the case of split events.

The concept of the center of gravity Xc of an X-ray event is introduced in order to determine the interaction position from the event pattern. Xc can be calculated from a signal output from the pixels in accordance with equation (9):

$$X_C = \frac{\sum D_n X_n}{\sum D_n} \quad (9)$$

where $X_n$ represents the nth pixel position.

Figure 10A:
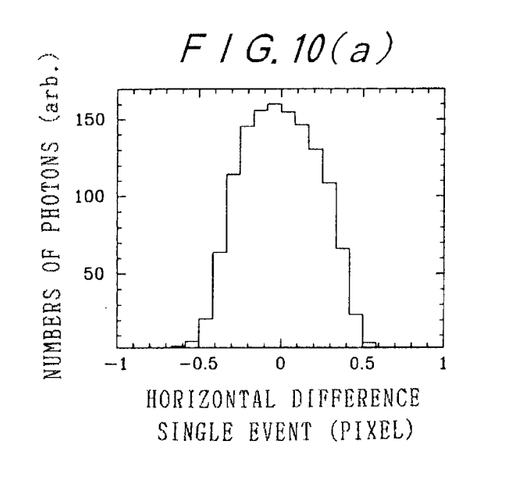
FIGS. 10(a)–10(d) are graphs relating to the embodiment of the present invention and showing position uncertainties of single events.
Figure 10B:
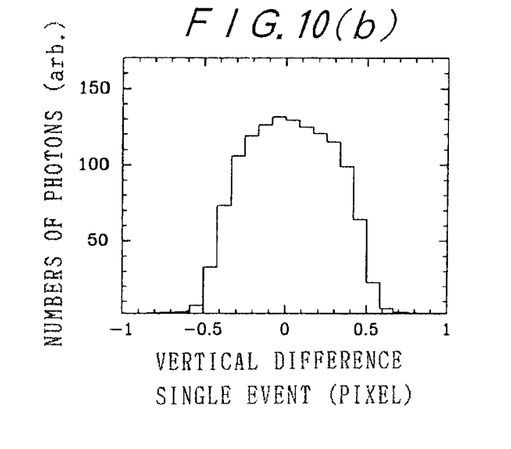
Figure 10C:
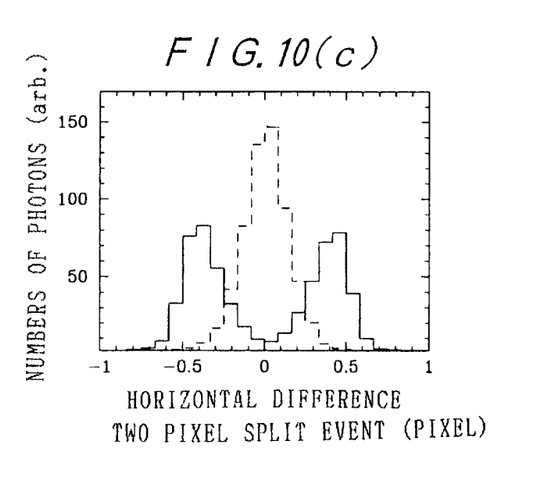
Figure 10D:
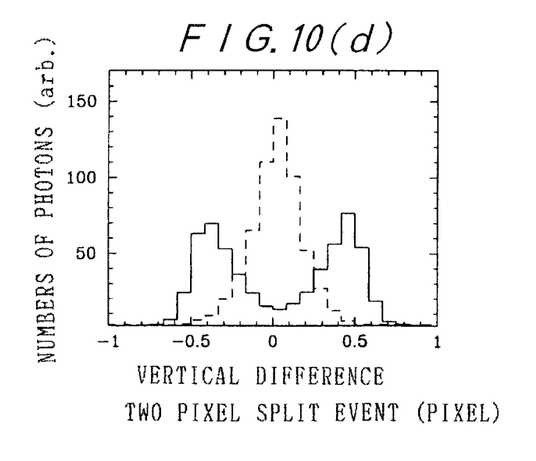

FIGS. 10(a)–10(d) also show, by means of dashed lines, the event distribution $D_{cg}$ according to the distance between the center of gravity of the event and the true interaction position. FIG. 10(a) shows the position uncertainty of single events along the X-axis; and FIG. 10(b) shows the position uncertainty of single events along the Y-axis. FIG. 10(c) shows the position uncertainty of split events along the X-axis; and FIG. 10(d) shows the position uncertainty of split events along the Y-axis. The solid line represents the distribution of $D_{event}$, and the dashed line represents the distribution of $D_{cg}$.

FIGS. 10(a)–10(d) show that $D_{cg}$ is identical to $D_{event}$ for single events, but $D_{cg}$ is not identical to $D_{event}$ for split events. By taking into account the uncertainty of the interaction position for single events, it can be said that the single event occurs at the pixel where the X-ray enters. In the two-pixel events, much finer distribution can be seen for $D_{cg}$ than for $D_{event}$. When a single Gaussian function is applied to the distribution of $D_{cg}$, a pixel size of 0.13 can be obtained for 1σ. That is, use of split events enables specification of the interaction position of X-rays with subpixel resolution.

These results clearly show that the center of gravity provides a more accurate interaction position than does the event pixel. When the center of gravity of the event is employed as the interaction position, the uncertainty is always better than 0.5 pixel size for any grade event. However, this does not hold true in the case where the event pixel is employed as the interaction position. In the single-pitch mesh experiment, the distance to the nearest mesh hole from the event pixel location is always 0.5 pixel size or smaller.

Previously, the event pixel was taken as the interaction position in the single-pitch mesh experiment. Therefore, the interaction position could not be uniquely specified, except in the case of single events. As a result, the left split two-pixel events (grade 3) and the right split two-pixel events (grade 4) could not be distinguished from each other. If the method for determining the interaction position of an X-ray by use of the center of gravity is employed instead of the event pixel, the interaction position can be uniquely determined.

As described above, in the present invention, the interaction position of an X-ray within a CCD pixel is unambiguously determined. This enables experimental confirmation that the event pixel coincides with the interaction position. The primary charge splits into the adjacent pixel only when the interaction position is sufficiently close to the pixel boundary.

The present invention provides a new method for determining the interaction position of X-rays by use of the center of gravity of the event. This method improves the determination accuracy of the interaction position of split events. The uncertainty of this method is only about 0.13 times pixel size. Furthermore, it becomes possible to determine the precise interaction position of the single event by use of either the event pixel or the center of gravity.

Therefore, the method according to the present invention enables determination of the interaction position of an X-ray not only for the case where a multi-pitch mesh is used but also for the case where a single-pitch mesh is used.

The method using the single-pitch mesh has a practical advantage in that a moire pattern is a direct expansion of RP. However, it is impractical to fabricate various types of meshes to fit various CCD pixel sizes.

The reason for this is that different CCDs employ different pixel sizes. If mesh hole spacing is equal to or larger than pixel size, the interaction position of an X-ray can be determined unambiguously. Therefore, the mesh used in the embodiment and having holes spaced at 48 µm can be applied to any CCD whose pixel size is smaller than 48 µm. Even if no moire pattern is obtained, an RP is obtained through identification of true parameter values.

As described above in detail, the conventional methods enables determination that "an X-ray signal is located some-where within a certain pixel." That is, when the pixel size is 10 μm, the accuracy in determining the position is ±5 μm.

By use of the present invention, the position of an X-ray can be determined with an accuracy of about ±1 μm. That is, the positional resolution is improved accordingly. Therefore, a thin line or the like formed by X-rays can be obtained more clearly as compared with conventional techniques.

The present invention is not limited to the above-described embodiments. Numerous modifications and variations of the present invention are possible in light of the spirit of the present invention, and they are not excluded from the scope of the present invention.

Industrial Applicability

As described above, the present invention enables analysis of X-rays and accurate determination of incident position, and therefore is preferably applied to the field of astronomy and other fields.

What is claimed is:

1. A method of determining an incident position of an X-ray detected by use of a CCD of a CCD camera onto which a parallel X-ray beam generated from an X-ray generator is radiated via a metal mesh disposed in front of the CCD, characterized in that
   (a) a multi-pitch metal mesh is disposed as the metal mesh; and
   (b) the incident position of the X-ray is determined on the basis of a ratio between a primary electron cloud produced by the X-ray spread over a plurality of pixels and a portion of the cloud existing in each of the plurality of pixels.

2. A method according to claim 1, characterized in that the accuracy in determining the incident position of an X-ray is about one-tenth of the pixel size of the CCD.

3. A method according to claim 1, characterized in that an interaction position is determined from an event pattern on the basis of the center of gravity of an X-ray event.

4. A method according to claim 3, characterized in that the center of gravity of an X-ray event is obtained on the basis of an output signal of a corresponding pixel.

5. An apparatus for determining an incident position of an X-ray detected by use of a CCD of a CCD camera onto which a parallel X-ray beam generated from an X-ray generator is radiated via a metal mesh disposed in front of the CCD, characterized by comprising:
   (a) an X-ray generator for obtaining a parallel X-ray beam;
   (b) a multi-pitch metal mesh disposed in front of the CCD and adapted to receive the parallel X-ray beam;
   (c) a CCD camera for photographing the CCD; and
   (d) means for determining the incident position of the X-ray on the basis of a ratio between a primary electron cloud produced by the X-ray spread over a plurality of pixels and a portion of the cloud existing in each of the plurality of pixels.

6. An apparatus according to claim 5, characterized in that the multi-pitch metal mesh has a large number of circular holes disposed at a pitch four times the pixel size of the CCD.

* * * * *